United States Patent [19]

Wiegers et al.

[11] 4,265,836
[45] May 5, 1981

[54] PROCESS FOR PRODUCING CIS-PENT-2-ENYL-1-CHLORIDE

[75] Inventors: Wilhelmus J. Wiegers, Red Bank; John B. Hall, Rumson, both of N.J.

[73] Assignee: International Flavors & Fragrances Inc., New York, N.Y.

[21] Appl. No.: 174,187

[22] Filed: Jul. 31, 1980

Related U.S. Application Data

[63] Continuation-in-part of Ser. No. 32,746, Apr. 24, 1979, abandoned.

[51] Int. Cl.$^3$ .............................................. C07C 21/04
[52] U.S. Cl. .................................................... 570/230
[58] Field of Search ..................................... 260/654 R

[56] References Cited

U.S. PATENT DOCUMENTS 2,404,235   7/1946   Kharasch ......................... 260/654 R

OTHER PUBLICATIONS

Mesnard and Miginiac, Compte Rendus Aced. Sc. Paris, t 277 (Oct. 8, 1973), pp. 657–570.
Kajiwara et al., "Isolation of Z-3-Hexenal in Tea Leaves, Thea Sinensis and Synthesis Thereof", Agr. Biol. Chem., 39(1) 243–247, 1975.

Primary Examiner—Patrick Garvin
Assistant Examiner—J. V. Howard
Attorney, Agent, or Firm—Arthur L. Liberman

[57] ABSTRACT

A process is described for the preparation of cis-pent-2-enyl-1-chloride according to the reaction:

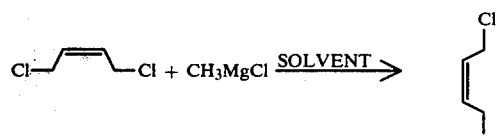

4 Claims, 2 Drawing Figures

IR SPECTRUM FOR EXAMPLE I.

PROCESS FOR PRODUCING CIS-PENT-2-ENYL-1-CHLORIDE

This application is continuation-in-part of application for U.S. Letters Patent, Ser. No. 032,746, filed on Apr. 24, 1979, now abandoned.

BACKGROUND OF THE INVENTION

Cis-pent-2-enyl-1-chloride is a valuable substance useful in the preparation of cis-jasmone which, in turn, is a valuable substance useful in the formulation of perfume materials. The cis-jasmone can be prepared according to the reaction:

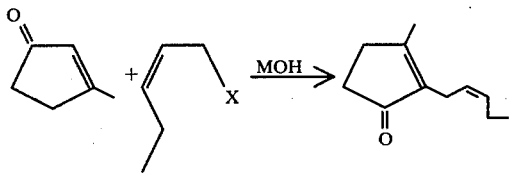

wherein X is chloro and wherein M is alkali metal. Such a reaction is more specifically exemplified in U.S. Pat. No. 4,045,489 issued on Aug. 30, 1977 wherein the reaction is carried out (1) using a "phase transfer agent" and (2) in a two phase system.

The reaction of a Grignard reagent with an alkenyl dihalide is well known in the prior art. Thus, a paper by Mesnard and Miginiac appearing at Compte Rendus Acad. Sc. Paris, T277 (Oct. 8, 1973) at pages 567–570 discloses, generically, the reaction sequence:

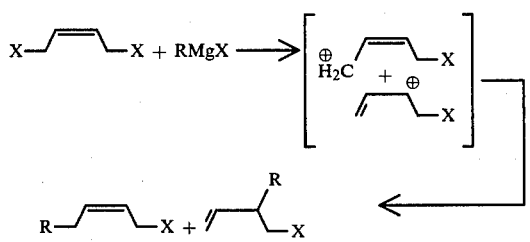

wherein X is halogen and wherein R is lower alkyl. Specifically exemplified is the reaction between methyl magnesium iodide and trans 1,4-dibromo-2-butene.

The specific reaction of our invention as described by the reaction scheme:

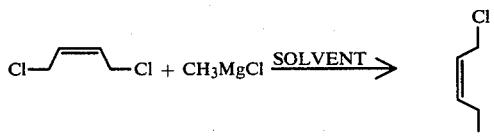

is not taught by Mesnard and Miginiac.

Thus, the Mesnard and Miginiac reference does not fulfill the need for producing a pure or substantially pure cis-pent-2-enyl-1-chloride, in one step without the need for an expensive physical separation step whereby the cis-pent-2-enyl-1-chloride is separated from the reaction mass. According to the teaching of Mesnard and Miginiac if cis-pent-2-enyl-1-chloride were produced it would be a minor product and 4-chloro-3-methyl-1-butene would be the major product.

Cis-2-penten-ol is produced from 1-chloro-4-hydroxy-2-butene by reaction with methyl magnesium bromide according to the teachings of Kagiwara et al, Agr. Biol. Chem., 39 (1), 243–247, 1975. The problems associated with reaction of a dihalide rather than the hydroxyl halide compound of Kagiwara et al are quite evident. Accordingly, the Kagiwara et al teaching is not predictive of the production of substantially pure cis-pent-2-enyl-1-chloride by the process of the instant invention.

Kharasch, U.S. Pat. No. 2,404,235 discloses a reaction of a vinyl halide and an aryl Grignard or aryl-alkyl Grignard reagent according to the reaction:

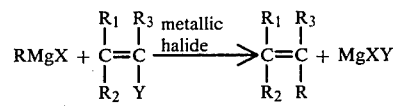

in which X is halogen, R is an aryl radical such as phenyl or anphthyl or an aryl-aliphatic radical such as benzyl and Y, $R_1$ and $R_2$ and $R_3$ are as follows:

Y is a halogen;

$R_1$ is hydrogen, lower alkyl, or aromatic;

$R_2$ and $R_3$ are selected from the group consisting of hydrogen and lower alkyl but are both hydrogen when $R_1$ is aromatic.

The Kharasch reaction is a reaction different in kind from the reaction of our process. The disclosure of the reaction of a vinyl halide and a Grignard reagent in general does not give rise to predictability of the reaction of an allyl halide and Grignard reaction as is the case in our process.

THE INVENTION

Figure 1:
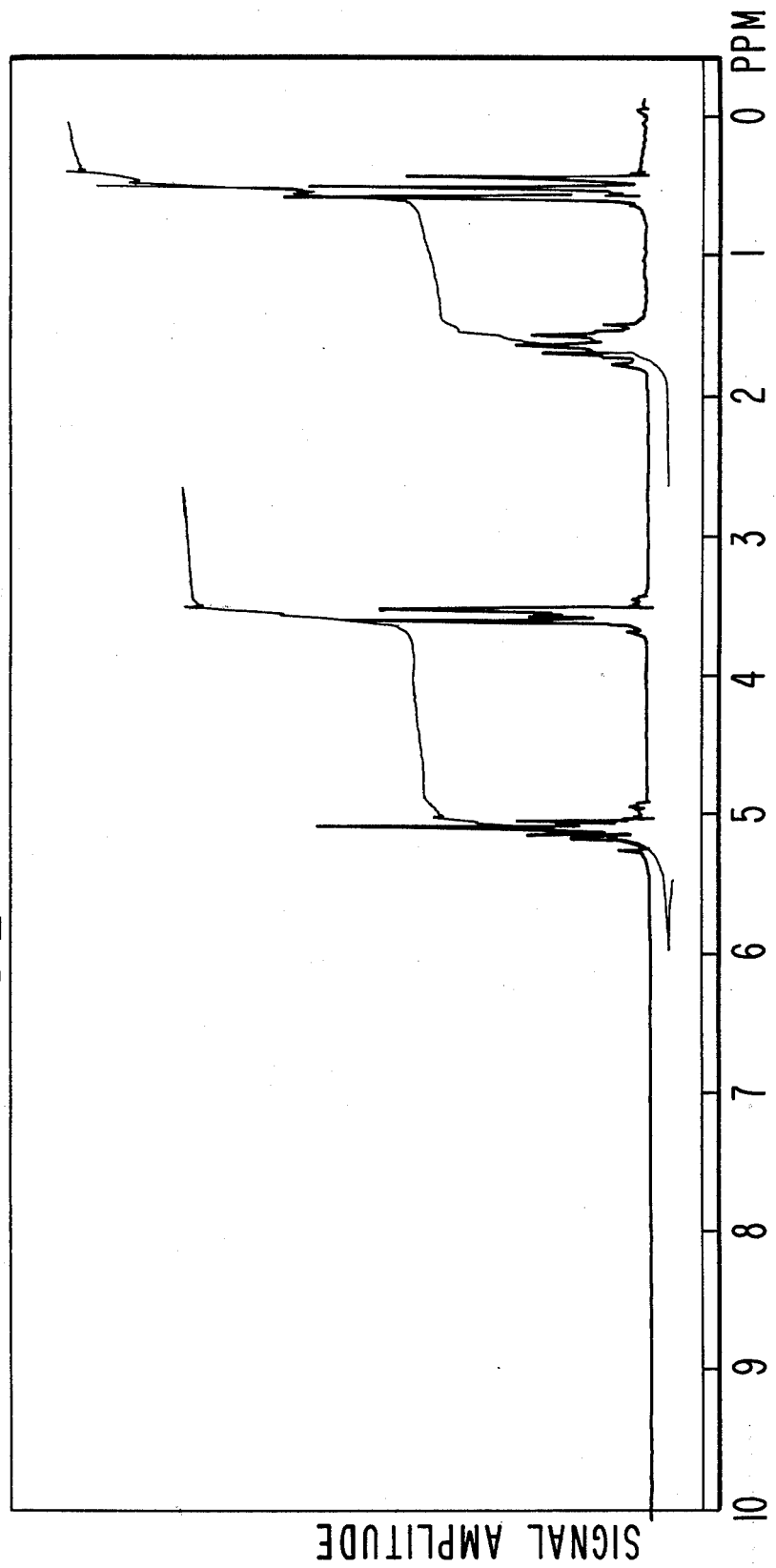
FIG. 1 is the NMR spectrum for the substantially pure cis-pent-2-enyl-1-chloride produced according to Example I.

The invention accordingly comprises the novel process and steps, specific embodiments of which are also described hereinafter by use of experiments and in accordance with what is now the preferred practice of the invention.

The process of our invention comprises reacting cis-1,4-dichlorobutene-2 with methyl magnesium chloride in the presence of one or more inert solvents. Thus, the invention is illustrated by the following reaction:

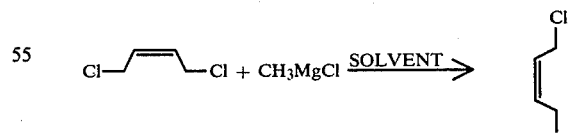

More specifically, our invention provides a process for the reaction of methyl magnesium chloride with cis-1,4-dichloro-butene-2, a valuable intermediate, for example, in the alkylation of 3-methyl-cyclopentenone to form cis-jasmone.

The reaction of our invention may be carried out in a solvent which is either of tetrahydrofuran, a mixture of tetrahydrofuran and benzene, a mixture of tetrahydrofuran and toluene, or diethyl ether. The diethyl ether solvent is preferred since it can easily be removed after the reaction.

The mole ratio between the methyl magnesium chloride and the cis-1,4 -dichloro-butene-2 may vary from about 1:1 up to about 3:1 with a mole ratio of methyl magnesium chloride:cis-1,4-dichloro-butene-2 of 3:1 being preferred.

The reaction temperature may vary from about 0° C. up to about reflux temperature with a reflux temperature being preferred. The reflux temperature used is a function of the particular solvent used. Thus, when a 50:50 mixture of tetrahydrofuran and benzene is used and the reaction is carried out at atmospheric pressure, the reflux temperature is 64°–68° C. When tetrahydrofuran, alone, is used, the reflux temperature is 55° C. at atmospheric pressure. When a 50:50 mixture of tetrahydrofuran and toluene is used, the reflux temperature is 75°–79° C. at atmospheric pressure; and when diethyl ether is used as a solvent, the reflux temperature is 38°–44° C.

There is no need to use a catalyst in the process of our invention and there is no need to operate at low temperatures in the process of our invention. Indeed, a catalyst should be excluded from the reaction mass since such catalyst actually interferes with the physical work-up of the reaction mass and subsequent reaction to produce the cis jasmone, an important perfumery compound.

It is preferred to add the methyl magnesium chloride to the cis-1,4-dichloro-butene-2 over a period of about 2–3 hours in order to obtain the highest conversion and yield.

The reaction pressure may be atmospheric but the reaction may, if desired, be run under pressure greater than atmospheric if desired without loss of yield of conversion.

After mixing of the solvent, methyl magnesium chloride and cis-1,4-dichloro-butene-2, the reaction mass may be stirred for a period of from about 1 hour up to about 15 hours with a period of additional stirring of from about 3 up to about 5 hours being preferred.

The reaction between the methyl magnesium chloride and the cis-1,4-dichloro-butene-2 effects the formation of a "Grignard complex" which is then hydrolyzed with a saturated aqueous solution of ammonium chloride or with dilute acetic acid. As a hydrolysis reagent, the dilute acetic acid is preferred (up to 3 molar).

Subsequent to the hydrolysis whereby the cis-pent-2-enyl-1-chloride is formed, the solvent is removed by fractional distillation and the crude cis-pent-2-enyl-1-chloride may be used as such or may be fractionally distilled again at atmospheric pressure or at reduced pressure.

Nothing in any prior art disclosures sets forth a procedure for preparation of a high purity cis-1,4-dichloro-butene-2 and the formation of such high purity cis-1,4-dichloro-butene-2 over a period of about 2–3 hours is commercially advantageous and unexpected and unobvious.

The following Example I serves to illustrate an embodiment of our invention as it is now preferred to practice it. Examples II and III illustrate the utility of the cis-pent-2-enyl-1-chloride produced according to the process of our invention as an intermediate to produce cis-jasmone. Example IV sets forth the utility as a perfume material of the resulting cis-jasmone. It will be understood that these Examples are illustrative and restricted thereto only as defined in the appended claims.

EXAMPLE I

PREPARATION OF CIS-PENT-2-ENYL-1-CHLORIDE REACTION

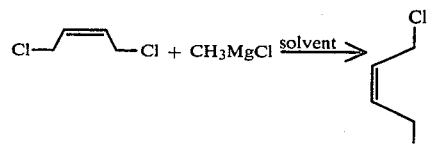

Into a dry 2 liter reaction flask equipped with condenser, addition funnel, stirrer, thermometer and thermo-watch are placed 140 grams of cis-1,4-dichloro-butene-2; 350 grams of tetrahydrofuran (400 ml.).

Over a 25 minute period a solution of 3 moles of methyl magnesium chloride in 350 ml tetrahydrofuran is added from the addition funnel to the reaction mass. After the addition of the methyl magnesium chloride solution, the reaction mass is stirred while progress of the reaction is monitored on GLC apparatus (conditions: 5% Carbowax column programmed at 50°–220° C. at 6° C. per minute). After 15 minutes the ratio of cis-pent-2-enyl-1-chloride: cis-1,4-dichloro-butene-2 is 19.5:76.0. After 1.5 hours the ratio is 41.3:57.3. After 2.5 hours the ratio is 60.4:38.7.

Over a 25 minute period, methyl magnesium chloride (a 3 molar solution in 100 ml tetrahydrofuran) is added to the reaction mass. 3 hours after the second addition, the ratio of product: starting material is 91.6:7.3.

Over a 15 minute period, saturated aqueous ammonium chloride solution is added to the resulting product (400 ml ). The reaction mass is stirred for a period of 30 minutes and 300 ml water is added thereto causing suspended solids to dissolve. The reaction mass is then washed with four 200 ml volumes of saturated sodium chloride solution. The reaction mass is then stripped of solvent and distilled after adding thereto 10 grams of Primol ® (registered trademark of Exxon Corporation of Linden, New Jersey, identifying a hydrocarbon mineral oil) yielding the following fractions:

| No. | Vapor Temp. | Liquid Temp. | Vac. mmHg | Wt. g. | Reflux Ratio |
|---|---|---|---|---|---|
| 1 | 22–26 | 33–43 | 100 | 9.1 | 4:1 |
| 2 | 47 | 58 | 100 | 4.1 | 4:1 |
| 3 | 54 | 64 | 125 | 6.1 | 4:1 |
| 4 | 55 | 65 | 125 | 9.0 | 4:1 |
| 5 | 55 | 70 | 125 | 10.0 | 4:1 |
| 6 | 56 | 79 | 125 | 11.0 | 4:1 |
| 7 |  | 25 | 125 | 3.0 | 4:1 |
| 8 | 45 | 93 | 5 | 6.2 | 4:L |

Figure 2:
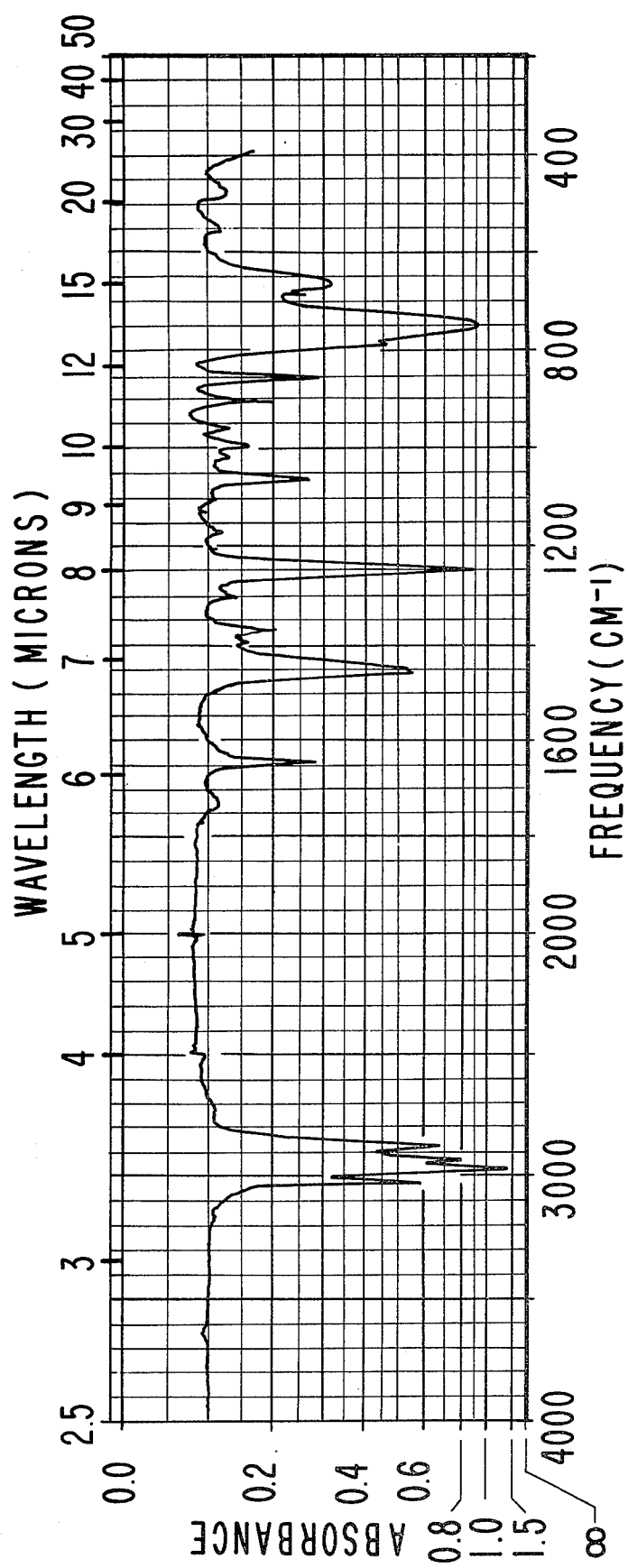
FIG. 2 is the infrared spectrum for the substantially pure cis-pent-2-enyl-1-chloride produced according to Example I.

Fraction 6 is analyzed using NMR and IR analysis. FIG. 1 is the NMR spectrum for fraction 6. FIG. 2 is the infrared spectrum for fraction 6.

Fractions 4–7 are bulked and used in the following Examples.

EXAMPLE II

PREPARATION OF CIS-JASMONE

Into a 250 ml reaction flask equipped with heating mantle, condenser, stirrer, thermometer and addition funnel is placed a solution of 21.3 grams of sodium hydroxide and 21.3 grams of water. Twenty grams of toluene and 1.5 grams of tricapryl methyl ammonium chloride (ALIQUAT 336®, produced by the General Mills Chemicals, Inc.) are then added to the mixture. The reaction mass is then heated to reflux (102° C.) and, over a one hour period, a mixture of 35 grams of cis-pent-2-enyl-1-chloride (produced according to Example I, bulked fractions 4–7) and 24.5 grams of 3-methyl cyclopentenone-2 is added to the reaction mass while refluxing. The reaction mass is then refluxed for an additional 4 hour period, after which time it is mixed with 100 ml cold water and transferred to a separator funnel.

The organic layer is separated, washed neutral and the solvent stripped off.

The residual oil is then retained for admixture with the reaction product of Example III prior to distillation.

EXAMPLE III

PREPARATION OF CIS-JASMONE

Into a 1 liter reaction flask equipped with heating mantle, condenser, thermometer, addition funnel and stirrer is placed a solution of 106.5 grams of sodium hydroxide in 106.5 grams of water. 100 Grams of toluene and 7.5 grams of tricapryl methyl ammonium chloride are then added to the mixture. The mixture is heated to reflux and over a 1 hour period, a mixture of 122.5 grams of 3-methyl cyclopentenone-2 and 175 grams of cis pent-2-enyl-1-chloride (produced according to Example I, bulked fractions 4–7) is added to the reaction mass. The reaction mass is then refluxed for a period of two hours, after which time 250 ml water is added thereto and the resulting mixture is transferred to a separatory funnel.

The organic layer is separated, washed neutral and the solvent is stripped off.

The residual oil is then bulked with the product of Example II and the resulting product is combined with 17 grams of Primol ®, 7 grams of triethanolamine and rushed over to yield the following fractions:

| Fraction No. | Vapor Temp. (°C.) | Liquid Temp. (°C.) | Vacuum mm | Weight (g) |
|---|---|---|---|---|
| 1 | 43–120 | 91–159 | 2.6 | 27.3 |
| 2 | 125 | 162 | 2.6 | 19.0 |
| 3 | 167 | 185 | 2.6 | 18.3 |
| 4 | 184 | 201 | 2.5 | 19.4 |
| 5 | 203 | 217 | 2.5 | 16.4 |
| 6 | 220 | 240 | 2.5 | 26.9 |

Fractions 1, 2 and 3 of the rushed over material, are then bulked and the bulked material is combined with 2 grams of Primol ® and Ionox ®. The resulting material is then fractionally distilled on a 12 plate Vigreaux column yielding the following fractions:

| Fraction No. | Vapor Temp. (°C.) | Liquid Temp. (°C.) | Vacuum mm | Weight (g) |
|---|---|---|---|---|
| 1 | 53 | 107 | 3.5 | 4.8 |
| 2 | 36 | 100 | 1.0 | 4.5 |
| 3 | 72 | 120 | 0.8 | 3.1 |
| 4 | 80 | 121 | 0.8 | 4.0 |
| 5 | 80 | 123 | 1.0 | 4.9 |
| 6 | 78 | 122 | 1.2 | 4.2 |
| 7 | 79 | 128 | 1.2 | 3.8 |
| 8 | 79 | 137 | 1.2 | 4.6 |
| 9 | 79 | 144 | 1.2 | 3.9 |
| 10 | 87 | 151 | 1.2 | 2.3 |
| 11 | 97 | 159 | 1.2 | 4.1 |
| 12 | 98 | 174 | 1.2 | 3.8 |
| 13 | 112 | 182 | 1.2 | 2.4 |

| Fraction No. | Vapor Temp. (°C.) | Liquid Temp. (°C.) | Vacuum mm | Weight (g) |
|---|---|---|---|---|
| 14 | 120 | 2.4 | 1.2 | 1.9 |
| 15 | 125 | 250 | 1.2 | 2.6 |

Fractions 6–9 are bulked, analyzed and evaluated, NMR, IR and Mass Spectral analyses yield the result that the product is 94% cis-jasmone having the structure:

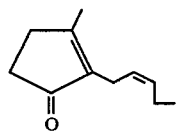

and the remainder, trans jasmone.

EXAMPLE IV

JASMINE PERFUME

The following mixture is prepared:

| Ingredient | Parts by Weight |
|---|---|
| Para Cresol | 1 |
| Acetyl Methyl Anthranilate | 20 |
| Farnesol | 4 |
| Cis-3-hexenyl benzoate | 30 |
| Nerolidol | 30 |
| Indol | 15 |
| Eugenol | 20 |
| Benzyl Alcohol | 40 |
| Methyl Linoleate | 40 |
| Jasmine Lactone | 20 |
| Dihydromethyl Jasmonate | 10 |
| Linalool | 150 |
| Benzyl Acetate | 400 |
| Abietyl Alcohol | 150 |
| Cis Jasmone (Produced according to Example III; bulked fractions 6-9) | 50 |

The cis-jasmone, produced according to Example III, imparts to this jasmine formulation the green, sweet, celery-like note so important to the jasmine perfume formulation.

What is claimed is:

1. A process for producing cis-pent-2-enyl-1-chloride according to the reaction scheme:

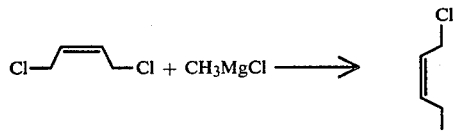

comprising the steps of reacting methyl magnesium chloride with cis-1,4-dichloro-butene-2 thereby forming a Grignard complex and hydrolyzing said Grignard complex, the reaction between the methyl magnesium chloride and the cis-1,4-dichloro-butene-2 being carried out in the absence of a catalyst and in the presence of a solvent selected from the group consisting of tetrahydrofuran, mixtures of tetrahydrofuran and benzene, mixtures of tetrahydrofuran and toluene, and diethyl ether; the mole ratio of methyl magnesium chloride:cis-1,4-dichloro-butene-2 being about 3:1; the temperature of reaction between the methyl magnesium chloride and the cis-1,4-dichloro-butene-2 being from about 0° C. up to reflux temperature; the methyl magnesium chloride being added to the cis-1,4-dichloro-butene-2 over a period of from about 2 up to about 3 hours; and carrying out the hydrolysis with a hydrolysis agent which is selected from the group consisting of aqueous ammonium chloride and dilute acetic acid; and then separating the reaction product, substantially pure cis-pent-2-enyl-1-chloride from the solvent by means of fractional distillation.

2. The process of claim 1 wherein the solvent is diethyl ether.

3. The process of claim 1 wherein the hydrolysis reagent is dilute acetic acid.

4. The process of claim 3 wherein the reaction product is separated from the solvent by distillation and the crude product is fractionally distilled.

* * * * *